United States Patent [19]

Sneider

[11] 4,262,669
[45] Apr. 21, 1981

[54] ACCORDION-STYLE SYRINGES, DOUCHES AND ATTACHMENTS THEREFOR

[76] Inventor: Vincent R. Sneider, 3422 Hallcrest Dr. NE., Atlanta, Ga. 30319

[21] Appl. No.: 868,847

[22] Filed: Jan. 12, 1978

Related U.S. Application Data

[60] Division of Ser. No. 700,838, Jun. 29, 1976, Pat. No. 4,068,662, which is a continuation-in-part of Ser. No. 592,037, Jun. 30, 1975, Pat. No. 4,014,332.

[51] Int. Cl.$^2$ ............................................. A61M 1/00
[52] U.S. Cl. .................................... 128/232; 128/251
[58] Field of Search ............... 128/232, 239, 251, 247, 128/231

[56] References Cited

U.S. PATENT DOCUMENTS

| | | | |
|---|---|---|---|
| 3,844,284 | 10/1974 | Schoenfeld et al. | 128/232 |
| 3,905,370 | 9/1975 | Lazdowski | 128/251 X |
| 3,968,797 | 7/1976 | Packer et al. | 128/232 |
| 4,052,986 | 10/1977 | Scaife | 128/251 X |
| 4,068,663 | 1/1978 | D'Alessandro | 128/232 |

Primary Examiner—John D. Yasko
Attorney, Agent, or Firm—Ralph R. Roberts

[57] ABSTRACT

This invention discloses improvements in accordion-style containers used with syringes, douches and the like. These improvements pertain to both prefilled, disposable, reusable syringe and douche containers and accessories used therewith. Among the novel constructions of containers is included a barium enema container in which the side is made with a flattened portion to provide a positive rest positon on a flat surface such as a floor with the outlet of the container in a positive elevated condition. A contoured end on a prefilled, disposable douche container is adapted to act as a plug or dam against an unwanted escape of fluid. A sliding plug of like contour may be carried on tubing which is used with a douche or enema container. Among the accessories is a nozzle having outwardly directed jet outlets adjacent and to the rear of a parabolic cone. Molded nozzles having large transverse outlets are also shown as is a stand and container providing an additional barium enema supply.

2 Claims, 24 Drawing Figures

ACCORDION-STYLE SYRINGES, DOUCHES AND ATTACHMENTS THEREFOR

CROSS REFERENCE TO RELATED APPLICATIONS

This patent application is a Divisional Application of my U.S. Patent Application Ser. No. 700,838, filed June 29th, 1976 which issued as U.S. Pat. No. 4,068,662 on Jan. 17th, 1978 which in turn is a continuation-in-part application of Ser. No. 592,037, filed June 30th, 1975 and entitled Disposable Syringe now U.S. Pat. No. 4,014,332.

BACKGROUND OF THE INVENTION

1. Field of the Invention

With reference to the classification of art as established in the United States Patent and Trademark Office the present invention is believed to be found in the general Class entitled, "Surgery" (Class 128) and more particularly in the subclasses therein entitled "syringe" (subclass 224) and in the subclass of "nozzle" (subclass 239) and also there is noted the subclass of "douches" (subclass 248) and in particular "vaginal douches" (subclass 251).

DESCRIPTION OF THE PRIOR ART

Douches and syringes and their accessories are well known and are widely used in hospitals and in the home. Among the patents pertaining to syringes are U.S. Pat. No. 2,784,716 to BROMAN on Mar. 12th, 1957; U.S. Pat. No. 2,811,968 to HYATT as issued on Nov. 5th, 1957; U.S. Pat. No. 3,177,871 to MEYERS as issued on Apr. 13th, 1965 and U.S. Pat. No. 3,626,939 as issued to MALTENFORT on Dec. 14th, 1971.

Improvements in prefilled vaginal douches are shown in the above-referenced application and prior patents. In the present invention there is shown a prefilled and sealed vaginal douche bottle whose sealed outlet prevents accidental and unwanted opening. After opening the container a fast thread enables an easy and rapid attachment of a nozzle. The accordion design of this container is also tapered so that the walls fold upon themselves to enable nearly one hundred percent expulsion of the premixed contents. The outlet end is contoured so that when pressed against the adjacent body opening the contoured end acts as and provides a plug against unwanted fluid escape.

A barium enema container having accordion side walls has a flattened side wall portion which provides a positive rest position on a horizontal surface enabling the outlet to be maintained in a stable elevated position. A fold-over cutoff is provided at the outlet to this container and two methods or positions for maintaining the tube in a held fold-over position are shown. An additional fluid supply container and stand for use with the barium enema container is shown. Nozzle improvements are also depicted.

SUMMARY OF THE INVENTION

This invention may be summarized at least in part with reference to its objects.

It is an object of this invention to provide, and it does provide, a sealed, prefilled syringe which has accordion-type side walls which are formed in a tapered pattern so that in use the container may be nearly one hundred percent emptied when the ends are moved nearly together. The outlet end of the container is contoured so as to provide a plug against unwanted escape of fluid from the opening in which is mounted the nozzle.

It is a further object of this invention to provide, and it does provide, a sliding plug which is a sliding fit on tubing as used with enema or douche containers. The plug is so contoured on the side toward the nozzle that when brought to or next to the nozzle and when pressed against the opening in which the nozzle is mounted unwanted escape of fluid from the opening is controlled or is largely prevented.

It is a further object of this invention to provide, and it does provide, a bellows-type enema container having accordion sides. The ends of this container have handles enabling manual manipulation for the opening and closing of the container. One side of the container is flattened to provide a positive rest portion which when placed on a flat surface such as a floor positions the outlet of the container in an elevated position. A stand adapted to support an additional fluid container while supporting the enema container is also provided.

It is also an object of this invention to provide, and it does provide, molded nozzles which are very useful with the several containers depicted.

In addition to the above summary the following disclosure is detailed to insure adequacy and aid in understanding of the invention. This disclosure, however, is not intended to cover each new inventive concept therein no matter how it may later be disguised by variations in form or additions of further improvements. For this reason there has been chosen a specific embodiment of the prefilled, accordion syringe, and enema container and attachment therefor as adopted for use with vaginal irrigation and showing a preferred means for making the several components used therewith. These specific embodiments have been chosen for the purposes of illustration and description as shown in the accompanying drawings wherein:

BRIEF DESCRIPTION OF THE DRAWINGS

In the following description and in the claims various details are identified by specific names for convenience. The names, however, are intended to be generic in their application. Corresponding reference characters refer to like members throughout the several figures of the drawings.

The drawings accompanying, and forming part of, this specification disclose certain details of construction but it should be understood that these structural details may be modified and that the invention may be incorporated in other structural forms than shown.

PRESEALED CONTAINER OF FIGS. 1 THROUGH 3

Figure 1:
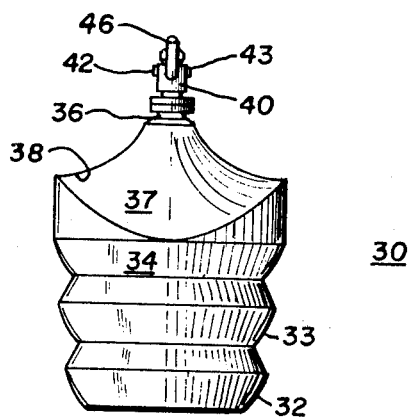
FIG. 1 represents a front view of a prefilled vaginal douche container which has a tear-away closure, and there is shown a fast thread on this end providing means for mounting on this end of a nozzle, this container has a tapered accordion side wall construction for virtual complete expulsion of the fluid contents and there is also provided a contoured end providing a fluid flow inhibiting means.
Figures 2, 3:
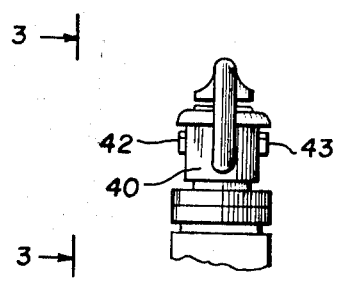
FIG. 2 represents a fragmentary enlarged side view of the nozzle attaching end of the container of FIG. 1, this view taken prior to the removal of the tear-away seal.
FIG. 3 represents a fragmentary, enlarged side view similar to that of FIG. 2 but transverse thereof.

Referring now to the drawings and in particular to FIGS. 1, 2 and 3, there is shown a small accordion-style container generally identified as 30. This container has two indentations forming the accordion pleat portions. The closed end or first pleat portion is identified as 32 and may be approximately seven-eighths of an inch long and about two and one-quarter inches in diameter. The next or second pleat portion 33 is about the same length and about one-quarter inch larger in diameter than portion 32. The upper or discharge end portion is identified as 34 and is about one-half inch long from the minimum pleat formation diameter to the maximum diameter of portion 33. The resulting diameter of the discharge end 34 is thus about two and seven-eighths inches. A tapered end configuration extends from this larger diameter 34 to a small neck portion 36. Two concave curves are employed in forming this tapered configuration. The major concave curve portion begins at about the termination of the accordion pleat portion 34 and is identified as 37. A shorter curve portion identified as 38 begins about three-quarters of an inch above the termination of the accordion pleat or taper 34 and flows into the reduced diameter neck 36 at the exit end of this container. Between these extremes, as exemplified by the concave curves 37 and 38, there is a blending of the curves in between so that a smooth curve transition is achieved.

At the neck portion 36 it is contemplated that a tight closure or cap member 40 is provided. On this cap member short, fast thread portions 42 and 43 are provided to retain a mounted nozzle when the sealing portion of the cap closure 40 is removed. Wing members 45 and 46 are a part of the cap closure and are molded with an intermediate portion 48 which is formed with reduced thickness portions so that when twisted a portion of the cap is freed and the container is then opened. When this container is to be opened the wing members 45 and 46 are grasped and turned causing the portion 48 to twist free and uncover the end of the container. A nozzle having appropriately formed threads or other mounting means is then mounted on the threaded end of this container.

USE AND OPERATION

Assuming that the prefilled syringe 30 is sealed with a one-time closure member 40, the deliberate opening of this container is achieved by turning portions 45 and 46, as well as the intermediate portion 48, to cause these portions to be sheared from their molded and sealed condition as provided by the cap closure. After the container has been opened, a nozzle is mounted on this threaded end. When and as the nozzle is entered into a body opening the contoured end is manipulated so as to engage the body skin and when pressed tightly thereagainst provides a plug or dam against unwanted fluid escape from the body opening. The container and the contoured plug end is then manipulated to regulate the rate of expulsion of the fluid from the opening. The thrust applied force to the container and the plug portion provides the amount of time of escape of the fluid from the body cavity.

NOZZLE AND FLUID CUTOFF OF FIGS. 4, 5 AND 6

Figure 4:
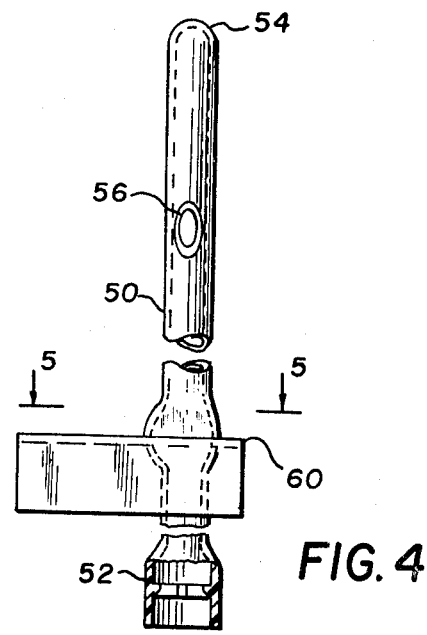
FIG. 4 represents a partial side view of a keyhole-type fluid cutoff and a soft nozzle having a side outlet.
Figure 5:
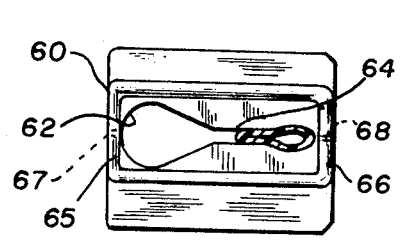
FIG. 5 represents a plan view taken on the line 5—5 of FIG. 4 and looking in the direction of the arrows.
Figure 6:
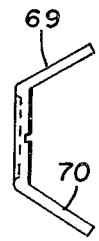
FIG. 6 represents an end view of the keyhole-type fluid cutoff of FIG. 5 and absent the tubing.

Referring next to FIGS. 4, 5 and 6, there is depicted a soft nozzle 50 having an enlarged end 52 which provides a snap-on or a screw-on fitting. A rounded end 54 may terminate a general tubing length and may be of soft tubing. About one and one-quarter to one and one-half inches from the end 54 is a side discharge hole 56 formed in this nozzle tubing length. In order to close or shut off fluid flow through this nozzle 50 there is provided a keyhole-type clamp generally indicated as 60. This clamp member is preferably made of plastic which may be extruded, molded or may be die cut and includes a keyhole-shaped opening 62 which terminates with a narrow slot 64. The combined aperture extends substantially the longitudinal length of this clamp. Small end portions 65 and 66 are provided at either end of this aperture and maintain a transverse support of the clamp 60. The sides of this clamp are turned downwardly at approximately sixty degrees to provide a manipulating means which is squeezed to cause a bending pressure to be brought upon the small end portions 65 and 66 of the clamp. These areas in the present instance have small or shallow grooves 67 and 68 formed in the mid or planar surfaces of the clamp 60.

It is contemplated in the manufacture of this item that the clamp may be an extruded piece of plastic with the grooves 67 and 68 formed as a part of the extrusion process. As a secondary punching operation a cut off of the extrusion may be combined to also provide the keyhole or tear-shaped opening 62 and the narrow slot 64. If desired, the slot 64 may be enlarged slightly at the right end side so that when a pressure is applied to the container a small amount of fluid may flow to the nozzle without breaking the clamp.

For a fuller description of this keyhole-type clamp 60 see my application, Ser. No. 592,037, filed June 30, 1975 and in particular note the description pertaining to FIGS. 7 and 8.

USE AND OPERATION OF THE NOZZLE AND CLAMP OF FIGS. 4, 5 AND 6

It is assumed that the nozzle 50 is used as a part of an enema or syringe assembly and that the attached tubing is of the desired length, generally two feet or more. The clamp member 60 is placed in position to insure that the fluid in the container is retained in the container and tubing until the time of expulsion. At the time of use the nozzle end 50 is positioned in the body opening, as desired, whereupon the user merely grasps the sloped sides 69 and 70 of the clamp 60 and urges them toward each other as to cause the weakened portions of ends 65 and 66 of the clamp to break into two portions. The fluid contents of the container and tubing are released and they may be forced through the soft nozzle 50, as desired.

SLIDING PLUG MEMBER OF FIG. 7

Figure 7:
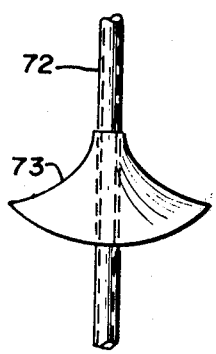
FIG. 7 represents a fragmentary side view of a length of tubing with a slidable plug thereon, the nozzle side of this plug is contoured so as to provide a closure that is pressed against the body opening in which is mounted the nozzle with escape of fluid past the plug largely prevented or controlled.

Referring next to FIG. 7, it is to be noted that upon a tubing length 72 there may be mounted a sliding plug in the nature of a light molded piece of plastic foam such as styrofoam or similar light plastic. This molded plug member is identified as 73. The contour of this plug member is preferably substantially identical to the contour formed on the discharge end of the container of FIG. 1. This contour side of the plug is placed upon the tubing and is faced toward the nozzle end so that in use and operation it is slid on the tubing to the desired position adjacent the end of the tubing. After a nozzle has been placed in the desired body opening the plug member may be placed against the surrounding skin of the opening to act as a dam and prevent unwanted loss or escape of fluid and the like.

ACCORDION CONTAINER OF FIGS. 8 AND 9

Figure 8:
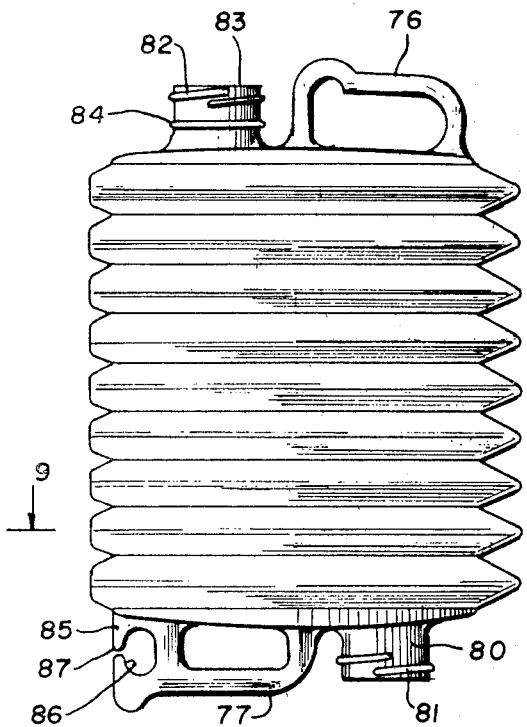
FIG. 8 represents a side view of a bellows-type enema bottle with an accordion side wall and with a portion of the side wall being formed with a flattened portion so that when laid on a flat support surface the outlet is maintained in a stable elevated position.
Figure 9:
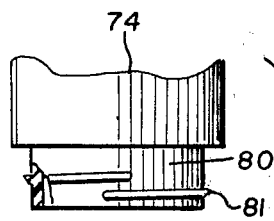
FIG. 9 represents a sectional view of the bottle or container of FIG. 8, this view taken on the line 9—9 thereof and looking in the direction of the arrows.

Referring next to FIGS. 8 and 9, there is depicted an accordion-type container 74, which, as shown, has its ends preferably molded with upper and lower finger-gripping handles or portions 76 and 77. These handles or handle portions provide means by which the accordion container may be manipulated for both expanding and collapsing of this container. To the lower end of the container 74 there is molded an outlet portion 80 on which is formed a thread 81. A like thread 82 is formed on the upper inlet 83 of the container. Immediately below the thread portion on this inlet end and for the purposes of supporting this container there is formed a rim or lip 84, to be hereinafter more fully described. On the lower handle portion 77 it is to be noted that a tubing grip or retainer 85 is formed and provides an aperture 86 in which is provided a slit or slot 87 for the passage therethrough of a length of tubing to be retained in a folded condition in this aperture during the storage and preliminary use of the container. It is to be noted that on this accordion-type container portion a flat area 88 is formed on the side of the container. This flat area is sufficient to allow the container to be laid with the outlet 80 in an elevated condition when this flat area of the container is placed or laid upon a flat surface such as a floor.

OUTLET OF FIGS. 10, 11 AND 12

Figures 10, 11:
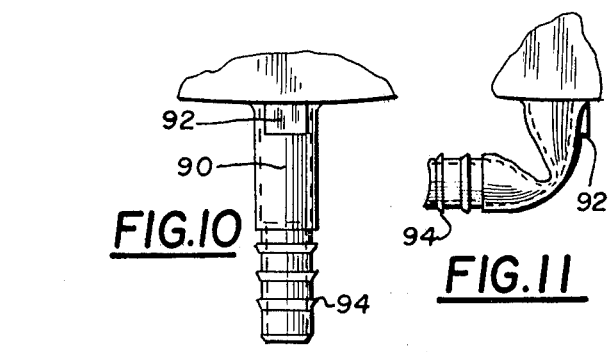
FIG. 10 represents a fragmentary side view of a fluid conduit outlet which is round in configuration and has a solid stiffening rib extending outwardly from one side and causing the tubing to pinch closed when bent at approximately a right angle.
FIG. 11 represents the fluid conduit shutoff of FIG. 10 with the conduit bent into flow shut off condition.
Figure 12:
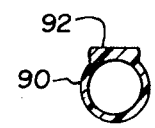
FIG. 12 represents a sectional view of the conduit of FIG. 10, this view taken on the line 12—12 thereof and looking in the direction of the arrows.

It is to be noted that instead of the screw-on outlet as provided on the container of FIG. 8, an alternate outlet 90 may be provided. This outlet is in the form of an attached round tubing having a stiffening rib 92 formed adjacent the outlet from the container. The tubing outlet end has barbed rings 94 which are adapted to hold a stretchable tubing which is expanded slightly for stretching and mounting thereon. As seen in FIG. 11, when the tubing portion 90 is bent to one side this stiffening rib 92 causes the tubing to close and provide a fluid cut off. FIG. 12 shows a typical cross section of the outlet 90 of FIG. 10. For a fuller discussion of this fold-over fluid cutoff see reference application and FIG. 20 therein.

ALTERNATE OUTLET AS SEEN IN FIG. 13

Figure 13:
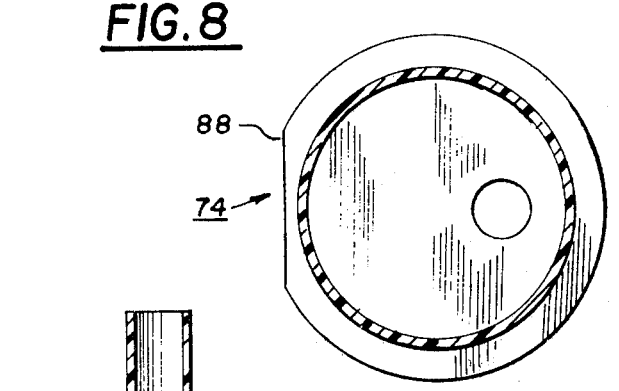
FIG. 13 represents a partly diagrammatic side and sectional view showing the fluid cutoff of FIG. 10 as adapted for screw mounting on a bottle or container such as in FIG. 8.

As seen in FIG. 13, the threaded outlet 81 of the container 74 may be used with a screw-on fitting. This screw-on fitting has a threaded ring 98 which is adapted to mate with the thread 81 of the outlet 80. In a mounted condition a loose plug piece 100, which is carried by the ring 98 of the screw-on piece 96, slides within the molded opening of the threaded outlet 81 and by means of the thread is drawn into a seated and tight inner connecting condition. The loose outlet plug piece 100 has a stiffening rib 102 which is similar to rib 92, shown in FIGS. 10 and 11. When the tubular portion of member 100 is bent sideways the tubing is caused to flatten and close and thus provides a fluid cutoff. Outlet aperture 104 formed in ring 98 is made a snap fit into a U-groove or V-groove 105 formed in the stem portion of the tubular member 100. Enlarged end 106 is carried inside the ring member 98. The barbed ring portion 108 is adapted to receive the end of the resilient, stretchable tubing to be attached to the end 109.

CLOSURE AND AIR INLET OF FIG. 14

Figure 14:
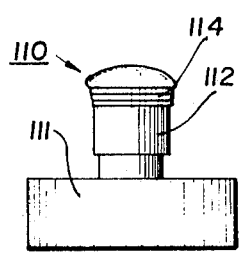
FIG. 14 represents a side view of a push-pull air shutoff valve and cap for inlets such as on the enema container of FIG. 8.

FIG. 14 represents an air inlet assembly 110 which may be provided at the inlet or filling end of the barium enema container. Air inlet assembly 110 may be similar to that shown in FIG. 18 of the above-identified application. A threaded cap 111 carries a longitudinal valve which has a finger gripping portion 112 by which the outer sleeve member 114 is moved outwardly. The intention of this valve is to provide a separately controllable air inlet to the interior of the container. This valve is opened and closed to the passage of air to the interior of the container as directed and desired by the operator. The closing of this valve also shuts off any flow of fluid.

USE AND OPERATION OF THE ENEMA ASSEMBLY OF FIGS. 8 THROUGH 14

It is contemplated that this enema container may initially contain a powder such as barium used for certain enemas. This powder is sealed by the air inlet valve assembly 110 and by the outlet valve such as shown in FIG. 13. When fluid is to be added the air inlet valve, shown in FIG. 14, is removed from the accordion container and the desired amount of liquid is now poured into the container. The valve assembly is then reapplied and tightened. The contents are shaken for mixing prior to the administration to the patient. When a rectal use is contemplated for the enema bag the nozzle of FIGS. 4 and 5 may be used. After proper placement of the nozzle the clamp is broken to allow fluid to pass through the tubing and to the end of the nozzle. If a bent-over fluid seal, as in FIGS. 8 and 13, is to be utilized then the bent-over portion of the tubing is caused to be released from its held condition and the tubing is straightened so that the fluid can flow therethrough. If this mixed fluid is to be transferred to the patient as by gravity then the air inlet valve 110 of FIG. 14 is opened by pulling the finger gripping outer sleeve 114 and moving it to permit air to enter the container.

If additional force is required for the administration of fluid to the patient then the air valve is closed by moving the finger gripping sleeve inwardly to cause the valve to close. The accordion container may then be manipulated to cause the ends to be moved toward each other with or without manipulating the end grip portions. If withdrawal of a portion of the enema solution from the patient is desired then the ends of the container are moved away from each other by manipulating the finger grips and pulling them outwardly. Prior to this expanding of the container the air inlet valve controlled by the finger gripping sleeve 114 is pushed to a closed position. The container may be placed upon the floor and the barium enema solution within the patient may be then withdrawn by negative pressure within the container and by gravity from the patient to the container. The flattened side portion of the container insures that the container is placed in a position whereby the outlet of the container is at the highest position to receive substantially all of the fluid which has entered into the patient.

NOZZLE OF FIGS. 15 AND 16

Figure 15:
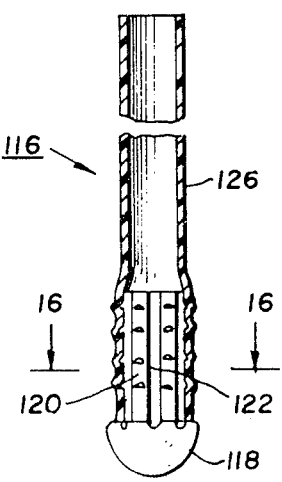
FIG. 15 represents a side view of a nozzle, partly in section, and showing the fluid outlets arranged to discharge transversely at the rear of a parabolic cone.
Figure 16:
FIG. 16 represents a sectional view taken on the line 16—16 of FIG. 15 and looking in the direction of the arrows.

Referring next to FIGS. 15 and 16, there is shown an assembled nozzle 116 in which an enlarged parabola-shaped end 118 is provided with a barbed stem portion 120. Into this stem portion there is formed longitudinal grooves 122 which terminate at and with radially disposed outlets 124. An outer sheath 126 encloses this stem 120 and provides the outer fluid guideway and retainer for the fluid flow directed up the grooves 122. The outer sheath is sufficiently resilient to mount an outlet such as that provided in FIGS. 10 and 13. If desired, the shaped end 118 may have a small stem portion which is mounted in a retained condition in a fluted tubular portion which is cut to length to provide the desired stem portion. The barbs in the stem may be formed as a secondary operation. Alignment of grooves 122 with the radial outlets 124 is required.

USE AND OPERATION OF THE NOZZLE OF FIGS. 15 AND 16

The nozzle of FIGS. 15 and 16 is mountable on any terminal end of tubing or outlet which has a proper size and stiffness. The fluid flow through the outer sheath member 126 proceeds up the grooves 122 and then outwardly from the radial outlet 124. The enlarged end portion 118 insures that at least a small portion of each and every outlet is uncovered while and when the nozzle is in the body opening. Whether as a douche or enema the nozzle having the enlarged end portion 118 insures that a flow from each outlet 124 will occur and a reasonable equal distribution of fluid will be delivered with a low pressure fluid flow.

THE AUXILIARY MOUNTING OF FIGS. 17 AND 18

Figure 18:
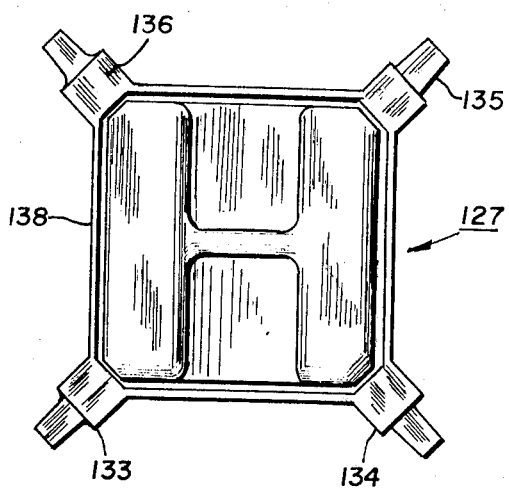
FIG. 18 represents the plan or end view looking down on the stand unit of FIG. 17.
Figure 17:
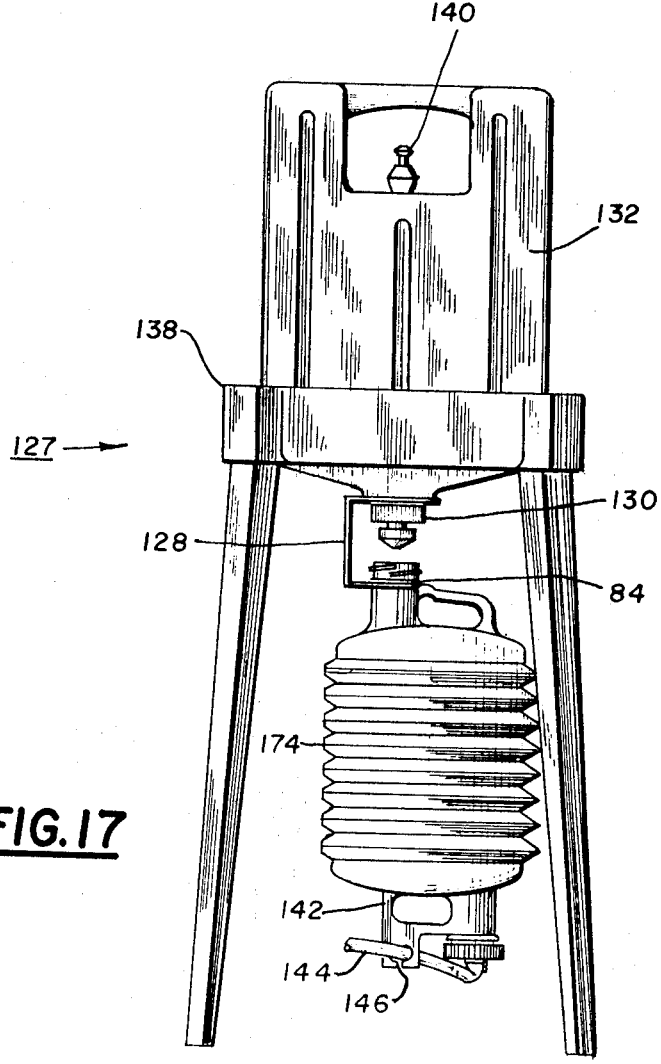
FIG. 17 represents a side view, partly diagrammatic, of the enema container of FIG. 8 as suspended by an auxiliary container in a stand arrangement.

Shown in FIGS. 17 and 18 is a metal or plastic stand 127 by which an auxiliary fluid supply may be provided or the entire fluid requirement may be fully supplied to the container of FIG. 8. It is to be noted that a metal C- or U-shaped clip 128 is provided and is slid onto the discharge end of the accordion-style container 74 to grip the annual ring 84. The upper end of this metal clip is also retained by a screw-on outlet fitting 129 fastened to a screw outlet 130 of a bottle or container 132. This stand 127 has preferably four legs identified as 133, 134, 135 and 136. These legs are attached to and carry an upper body 138 which receives a plastic container of rectangular configuration identified as 132. This container 132 may have an air inlet valve 140 to control the flow of fluid. This air inlet valve is preferably similar to the valve assembly 110 shown in FIG. 14.

Shown on the bottom of this container 174 is an alternate configuration for retaining the plastic tubing which is preferably mounted to the threaded outlet of the container by means of the fitting such as shown in FIG. 13. This tubing portion of the fluid outlet is bent at a right angle to provide a fluid cutoff and then is brought into a mounted condition in a depending portion 142 of a handle 77 in the container 174. In portion 142 is formed an aperture 144 and a slot 146. In use it is contemplated that the contents of the barium bag or container 74 will be mixed in accordance with the need or requirement of the user. If additional fluid is required then by use of the metal or plastic stand 127 the supplemental filled container 132 can supply container 174 positioned below the supplemental container by a C-clip 128. This accordion-style container is mounted in place below the outlet of the upper container or bottle 132. The separate fluid upper container may have a screw outlet 130 and fitting 129 by which from the bottom of container 132 the flow is controlled. This container 132 may have an upper regulated air inlet valve 140 similar to that shown in FIG. 14. In use the nozzle and tubing are released from the depending portion of the container. The nozzle is placed in position in the body opening of the patient. Usually this is a rectal opening and a contoured plug 10, as shown in FIG. 7, may be utilized. During use as the fluid supply in the container is depleted an additional fluid is supplied from the stand container 132 by opening the lower valve 129 and manipulating the air inlet valve 140 so that a fluid flow from the lower end of the supplemental stand container is controlled. The barium enema container 10 has a flat side so that when separated from the stand and auxiliary supply the accordion-style container can be laid on its side to receive the return flow of fluid from the enema nozzle.

AUXILIARY PRESSURE MEANS AS SEEN IN FIG. 19

Figure 19:
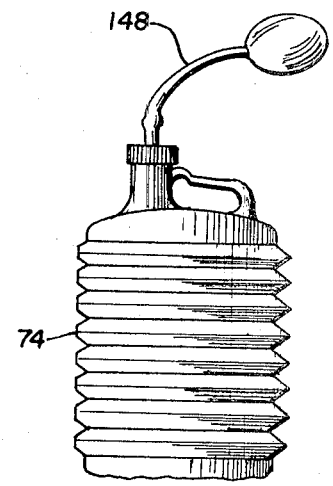
FIG. 19 represents a side view, partly fragmentary and showing the enema container of FIG. 8 with a pump attached to the inlet end of the container.

As seen in FIG. 19 it is to be noted that the threaded opening of the barium enema bag of FIG. 8 may be provided with a tubular outlet to which is mounted an air pressure pump 148. This pump may be like that used in the taking of blood pressure. This bulb-type pump is commonly available and may implement increases in pressure in the container of one hundred inches of mercury and more. Such a pressure when applied to the plastic container causes the fluid flow of the enema solution to progress further and faster than when pushed or advanced by gravity.

SOFT NOZZLES OF FIGS. 20 AND 21

Figure 20:
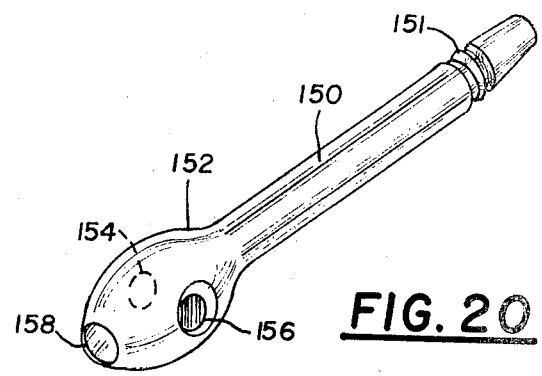
FIG. 20 represents a fragmentary view of a molded nozzle in which the major outlets are transverse of the normal axis.
Figure 21:
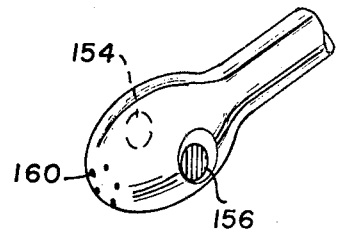
FIG. 21 represents a fragmentary view similar to that of FIG. 20 but showing an alternate method of molding the outlets.

Referring next and finally to FIGS. 20 and 21, there is depicted an enlarged nozzle which may be made out of a soft plastic. As shown, the nozzle has the open end adapted to receive the end of a rubber tubing. This tubing may or may not have a barbed adapter or portion 151 by which this tubing may be attached in a stretched and fluid-tight condition. As shown, it is contemplated that the nozzle of FIG. 20 has a shank portion 150 which is enlarged at end 152 to provide a discharge of the fluid. This end has two transverse holes 154 and 156 formed in the sides of this enlarged spherical portion. If desired, the end of the spherical nozzle may have a single forwardly directed outlet 158. In FIG. 21 is depicted the nozzle of FIG. 20, however, in addition to and having the side or transverse outlets 154 and 156 the nozzle end foregoes the large single forward opening of FIG. 20 and instead provides a plurality of small holes 160 which direct a forward spray of the fluid when the nozzle is filled with pressurized fluid.

ALTERNATE CONSTRUCTION OF ACCORDION CONTAINER OF FIGS. 22, 23 AND 24

Figure 22:
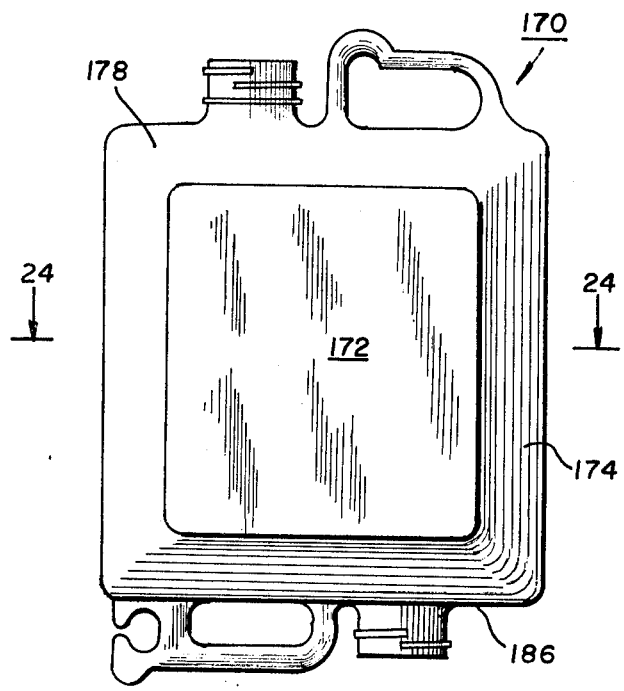
FIG. 22 represents a side view of an alternate construction of a barium enema container in which the pleated construction of the accordion side members are arranged to collapse longitudinally to enable a flat folding of the container for storage and shipping.
Figure 23:
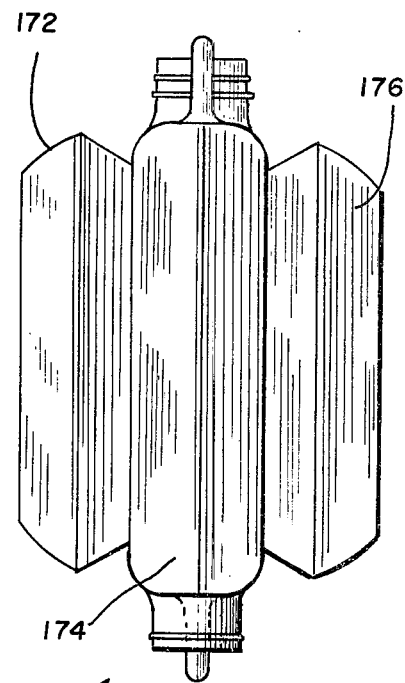
FIG. 23 represents an end view of the alternate construction as shown in the container of FIG. 22.
Figure 24:
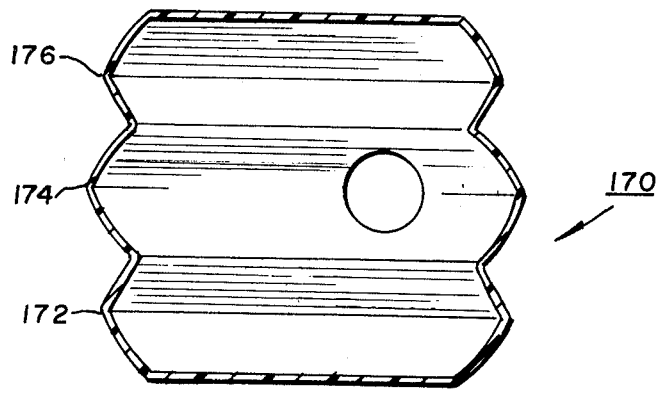
FIG. 24 represents a sectional view taken on the line 24—24 of FIG. 22 and looking in the direction of the arrows.

Referring next and finally to FIGS. 22, 23 and 24, there is shown an alternate enema container construction generally identified as 170. This container is contemplated to be of a large capacity such as the containers described in conjunction with FIGS. 8, 17 and 19. In this alternate configuration there is provided longitudinal rather than convolutions transverse of the container axis. The longitudinal convolutions, as shown, are three in number and identified as 172, 174 and 176 although many more can be provided, if desired. A top or entry end 178 and an outlet end 180 may have handle portions and the apertures as described in connection with the containers in FIGS. 8, 17 and 19, above noted.

The longitudinal pleats of the alternate container 170 allow the flat folding of the container for shipping. The container may or may not have powder therein prior to the final addition of fluid to the container at the time of use. A container having longitudinal pleats may also have a thinner wall to enable a closer folding while the filled container will stil have manipulative control. It is also contemplated that when packed for shipment, the longitudinally pleated container 170 less the fluid will be sufficiently flexible to allow the two end portions to be manipulated to require only a minimum occupied space.

Terms such as "left", "right", "up", "down", "bottom", "top", "front", "back", "in", "out" and the like are applicable to the embodiments shown and described in conjunction with the drawings. These terms are merely for the purposes of description and do not necessarily apply to the position in which the containers and attachments may be constructed or used.

While particular embodiments of the several accordion-style containers and nozzles have been shown and described it is to be understood that modifications may be made within the scope of the accompanying claims and protection is sought to the broadest extent the prior art allows.

What is claimed is:

1. A prefilled accordian-style container for vaginal douches, enemas and the like, said container including: (a) a flexible container of a generally accordian configuration and having in-folding sides having a tapered configuration enabling a user to substantially empty the container of the fluid contents when the smaller closed end is brought very near the outlet of the container; (b) a contoured outlet end formed on the container so as to have a blend of concave curved forms extending from a major to a minor length and vice versa, this contoured outlet end adapted to engage a body opening and when pressed tightly thereagainst to provide a plug preventing unwanted fluid from escaping from said body opening, and (c) a closed discharge opening provided on the discharge outlet of the container, this closure having manipulative removing means which includes a sealed one-time closure cap and there is provided fast thread portions which remain with and on the discharge opening after the seal has been removed, these thread portions facilitating the mounting of a nozzle, tubing and the like on said uncovered discharge end.

2. A prefilled accordion-style container as in claim 1 in which the contoured outlet end is on the larger end of the tapered configuration.

* * * * *